United States Patent
Hleihil et al.

(10) Patent No.: US 9,833,337 B2
(45) Date of Patent: Dec. 5, 2017

(54) BONE DEVICE WITH MULTIPLE SLIDING EXPANSION MEMBERS

(71) Applicant: Expanding Orthopedics Inc., Memphis, TN (US)

(72) Inventors: Jaffar Hleihil, Jish (IL); Mark M Levy, Raanana (IL); Eran Ishay, Tel Aviv (IL); Assaf Guy, Allone Abba (IL); Onn Levy, Kiryat Yam (IL)

(73) Assignee: Expanding Orthopedics Inc., Memphis, TN (US)

( * ) Notice: Subject to any disclaimer, the term of this patent is extended or adjusted under 35 U.S.C. 154(b) by 0 days.

(21) Appl. No.: 15/361,431

(22) Filed: Nov. 27, 2016

(65) Prior Publication Data

US 2017/0151063 A1  Jun. 1, 2017

Related U.S. Application Data

(60) Provisional application No. 62/260,348, filed on Nov. 27, 2015.

(51) Int. Cl.
| | |
|---|---|
| A61F 2/44 | (2006.01) |
| A61F 2/46 | (2006.01) |
| A61F 2/30 | (2006.01) |

(52) U.S. Cl.
CPC .......... *A61F 2/447* (2013.01); *A61F 2/4611* (2013.01); *A61F 2002/3055* (2013.01); *A61F 2002/30428* (2013.01); *A61F 2002/4475* (2013.01)

(58) Field of Classification Search
CPC ............... A61F 2/447; A61F 2/4611; A61F 2002/30428; A61F 2002/3055; A61F 2002/4475
USPC ............................ 623/17.11–17.16
See application file for complete search history.

(56) References Cited

U.S. PATENT DOCUMENTS

| | | | | |
|---|---|---|---|---|
| 6,332,895 B1 * | 12/2001 | Suddaby | ............... | A61F 2/4455 623/17.11 |
| 2004/0162618 A1 * | 8/2004 | Mujwid | .................. | A61F 2/447 623/17.15 |
| 2007/0123987 A1 * | 5/2007 | Bernstein | .................. | A61F 2/44 623/17.11 |
| 2008/0058930 A1 * | 3/2008 | Edie | .......................... | A61F 2/44 623/17.11 |
| 2014/0188225 A1 * | 7/2014 | Dmuschewsky | ....... | A61F 2/447 623/17.16 |

\* cited by examiner

*Primary Examiner* — Pedro Philogene
*Assistant Examiner* — David C Comstock
(74) *Attorney, Agent, or Firm* — Dekel Patent Ltd.; David Klein

(57) ABSTRACT

A cage device includes a first support member which has a bone contact surface and from which depend side surfaces that are provided with ratchet teeth. The first support member ratchets with a ratchet member, which in turn ratchets with a ratchet wall, such that the first support member and the ratchet member are movable independently of each other and form a multiple sliding mechanical mechanism.

14 Claims, 4 Drawing Sheets

BONE DEVICE WITH MULTIPLE SLIDING EXPANSION MEMBERS

FIELD OF THE INVENTION

The present invention generally relates to devices and methods for spinal fusion or other spinal techniques and particularly to a bone device, such as an intervertebral cage with multiple sliding support members, such as multiple ratcheting expansion members.

BACKGROUND OF THE INVENTION

Spinal fusion surgery employs different devices for achieving fusion of two or more vertebrae. For example, intervertebral cages are inserted in the disc space, as spacers, to improve the anterior column stability, preserve the disc space height and to contain bone graft in dedicated chambers to enhance the fusion process. In some cases supplementary screws, in the facets, pedicles or in the vertebral body from the anterior or lateral sides, are added to increase the stability. Some intervertebral cages are made of a single segment device, whereas others have more than one cage to cover more surface. Multiple segments may be attached with hinges, pivots or turning points to be able to cover more of the surface with only one device.

Intervertebral cages should provide a wide foot print for contact surface with both vertebrae endplates (superior and inferior). The cages should be placed preferably in the periphery of the disc space and should be able to fit the disc space height. Some cages provide expansion mechanisms for adjusting the height to fit the disc space height. Height adjustment is sometimes complemented with correction of lordosis by providing some angulation according to the location. In other cages, horizontal expandable mechanisms are provided for expansion transverse to the height. However, locking the expandable mechanism for vertical (height) or horizontal expansion may present a challenge due to the physiologic forces involved.

U.S. Pat. No. 6,332,895 describes an expandable intervertebral implant that includes a pair of semi-cylindrical shells, which are distracted inside an intervertebral space that has been appropriately prepared for fusion from an anterior approach. The semi-cylindrical shells have lateral wings which sit juxtaposed to the end plates of the vertebral body to provide a large surface area for adjacent end plate support. Each wing makes up at least 20% of the width of the implant, preferably at least 25%. The shells are distracted with an expandable installation tool and the shells are held apart by ratchets or corrugations in their side walls to permit optimal tensioning of the annular support ligaments, and hence immediate stability. The installation tool is then unscrewed and disengaged, leaving the component parts as a stable assembly that can be packed with bone to promote osseous union.

SUMMARY OF THE INVENTION

The present invention seeks to provide a bone device, such as an intervertebral cage with multiple sliding support members, such as multiple ratcheting expansion members. For example, the device may be a single or multiple segment cage for use in the intervertebral disc space, vertebral body or other bone. The cage includes an array of sliding mechanical mechanisms or ratchet-like arrangements to allow expansion and locking in one or more directions. The surfaces of the cage that come into contact with the endplates of the vertebrae can be parallel or non-parallel with any surface finish. The shapes of the contact surfaces can be square, circular, rectangular or crescent (kidney-like) shaped.

The expansion mechanism is based in a multiple sliding mechanical mechanism, ratchet-type or ratchet-like arrangement built in or attached to the cage that can be actuated mechanically, manually or assisted by any hydraulic, pneumatic or motorized means. The mechanical mechanisms can work in the same or in opposite directions in the same plane resulting in expansion and an increased cage height. In other cases the ratchet mechanisms can work in opposite or other directions in different planes, producing expansion in more than one direction. Furthermore, ratchet mechanisms can be used in non-parallel directions producing expansion and locking in one direction and gain of additional support in the opposite direction. Combinations of these cases can be found in the description below.

The devices can be made of any medical compatible material for bone utilization, such as but not limited to, titanium, PEEK (polyetheretherketone), polymers, or any other metal, natural or synthetic material. The surfaces of such devices may be regular or irregular, including surfaces that may enhance attachment to bone.

There is thus provided in accordance with a non-limiting embodiment of the present invention a cage device including a first support member which has a bone contact surface and from which depend side surfaces that are provided with ratchet teeth, wherein the first support member ratchets with a ratchet member, which in turn ratchets with a ratchet wall, such that the first support member and the ratchet member are movable independently of each other and form a multiple sliding mechanical mechanism.

In accordance with a non-limiting embodiment of the present invention ratchet elements of the first support member and the ratchet member are all oriented in same directions, thereby permitting movement in one direction only.

In accordance with a non-limiting embodiment of the present invention ratchet elements of the first support member and the ratchet member are not oriented in same directions.

In accordance with a non-limiting embodiment of the present invention the ratchet member includes a second support member, and the first support member and the second support member are ratcheted with each other by means of one or more ratchet walls extending from the second support member.

In accordance with a non-limiting embodiment of the present invention the first support member ratchets telescopically with the ratchet member.

In accordance with a non-limiting embodiment of the present invention the first support member ratchets telescopically with a first internal ratchet member and the first internal ratchet member ratchets telescopically with a second internal ratchet member.

Alternatively, the first support member ratchets non-telescopically with the ratchet member.

In accordance with a non-limiting embodiment of the present invention there is an internal ratchet transverse to the first support member. The internal ratchet may include a ratchet pawl that ratchets with a longitudinal ratchet bar. The longitudinal ratchet bar may be formed with a window and the pawl may engage the ratchet bar in teeth formed in the window.

BRIEF DESCRIPTION OF THE DRAWINGS

The present invention will be understood and appreciated more fully from the following detailed description taken in conjunction with the drawing in which.

DETAILED DESCRIPTION OF EMBODIMENTS

Figure 1A:
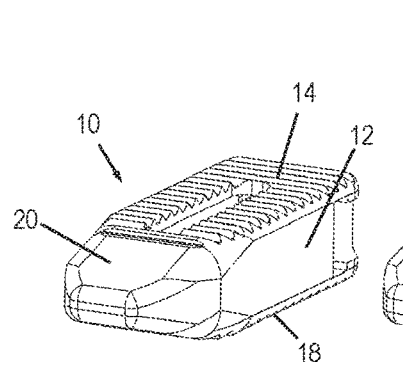
FIGS. 1A-1C are simplified illustrations of a cage device, constructed and operative in accordance with a non-limiting embodiment of the present invention, respectively in contracted, partially expanded and fully expanded orientations.
Figure 1B:
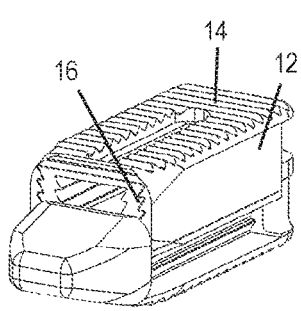
Figure 1C:
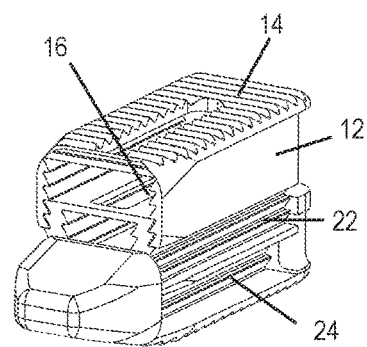

Reference is now made to FIGS. 1A-1C, which illustrate a cage device 10, in accordance with a non-limiting embodiment of the present invention.

Cage device 10 includes a first support member 12, which has a bone contact surface 14 (which may be roughened or otherwise treated for enhanced adhesion to bone), from which depend side surfaces that are provided with (internal) ratchet teeth 16. Cage device 10 includes a second support member 18 opposite and parallel to the first support member 12. In other embodiments, the two support members can be non-parallel. Support members 12 and 18 can be planar as shown, but alternatively may have other shapes, such as but not limited to, crescent, round, oval, trapezoid or any other shape, wherein the ratchet mechanism is disposed between the support members for their expansion. Cage device 10 may include a tapered nose section 20 for assisting insertion in the disc space or other places.

At the rear of the device, opposite the tapered nose section 20, a coupling port 29 (seen in FIGS. 3A-3B) is provided for inserting therein an insertion tool, distraction or expansion tool or any other instrument which may be needed for a particular medical procedure, such as for introduction of bone graft. Coupling port 29 may include, without limitation, a click-on connection, a threaded aperture, a bayonet connector, a pressure locking section or any other suitable and releasable connection between the device and the instrument. An example of an expansion tool is described below with reference to FIG. 8, and an insertion tool is described below with reference to FIGS. 9A-9D.

The first support member 12 ratchets with (the outer teeth of) an internal ratchet member 22, which in turn ratchets with an internal ratchet wall 24. Thus, first support member 12 and internal ratchet member 22 are movable independently of each other and form a telescopic double sliding mechanical mechanism (or ratchet-like mechanism). In this embodiment, the ratchet elements are all oriented in the same direction, thereby permitting movement in one direction only. The elements are locked at any position, due to the ratcheting.

The first support member 12 and internal ratchet member 22 may be moved manually or with a tool, such as but not limited to, a manual lever, electric, hydraulic or pneumatic motor (e.g., which operates a cam to move the members), or any other suitable means.

Figure 2A:
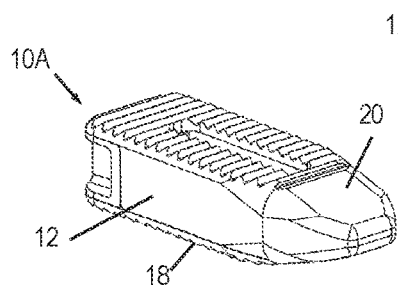
FIGS. 2A-2B are simplified illustrations of a cage device, constructed and operative in accordance with another non-limiting embodiment of the present invention, respectively in contracted and expanded orientations.
Figure 2B:
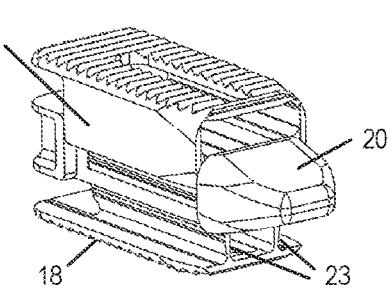

Reference is now made to FIGS. 2A-2B, which illustrate a cage device 10A, constructed and operative in accordance with another non-limiting embodiment of the present invention, with like elements being designated by like numerals. In this embodiment, the internal ratchet member 22 is missing and the second support member 18 is used as the ratchet member 22. The tapered nose section 20 remains central between the first support member 12 and the second support member 18, whether the device is contracted or expanded. In this embodiment, first support member 12 and second support member 18 are ratcheted with each other by means of one or more ratchet walls 23 extending from second support member 18. The ratchet elements are not oriented in the same direction; thus, during expansion, first support member 12 and second support member 18 move in opposite directions to each other.

Figure 3A:
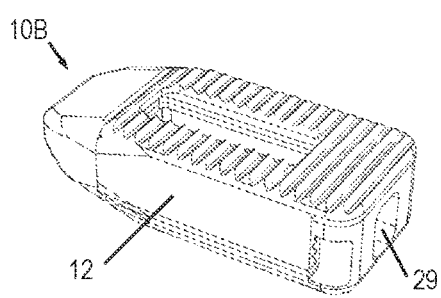
FIGS. 3A-3B are simplified illustrations of a cage device, constructed and operative in accordance with another non-limiting embodiment of the present invention, respectively in contracted and expanded orientations.
Figure 3B:
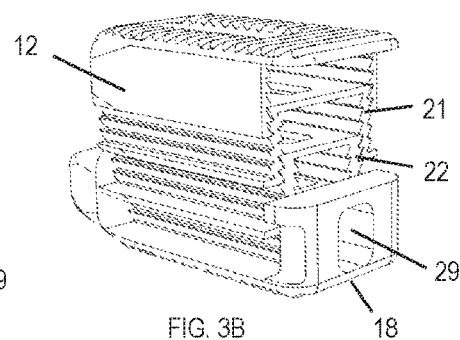

Reference is now made to FIGS. 3A-3B, which illustrate a cage device 10B, constructed and operative in accordance with another non-limiting embodiment of the present invention, with like elements being designated by like numerals. In this embodiment, two internal ratchet members 21 and 22 are provided so that first support member 12 ratchets telescopically with the first internal ratchet member 21 and the first internal ratchet member 21 ratchets telescopically with the second internal ratchet member 22, resulting in even more height gain after expansion. Thus, this embodiment has a triple ratchet mechanism, all in the same direction.

Figure 4A:
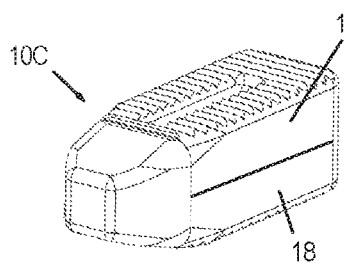
FIGS. 4A-4B are simplified illustrations of a cage device, constructed and operative in accordance with another non-limiting embodiment of the present invention, respectively in contracted and expanded orientations.
Figure 4B:
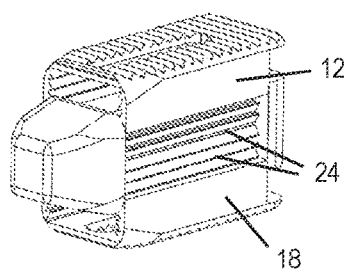

Reference is now made to FIGS. 4A-4B, which illustrate a cage device 10C, constructed and operative in accordance with another non-limiting embodiment of the present invention, with like elements being designated by like numerals. In this embodiment, the double ratchet mechanism is not arranged in a telescopic way but arranged one on top of the other, in opposite directions, sharing one ratchet wall 24 which has one portion (typically, but not necessarily, the upper half) with engaging (ratcheting) sections facing in one direction and another engaging portion facing the opposite direction. The central common ratchet wall 24 faces outwards, and the sides of expanding members 12 and 18 overlie the outer surface of wall 24.

Figures 5A, 5B:
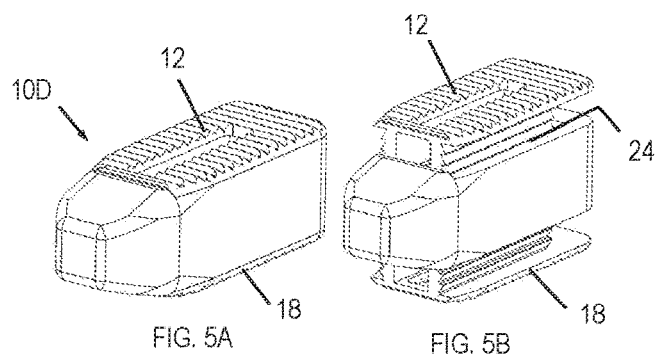
FIGS. 5A-5B are simplified illustrations of a cage device, constructed and operative in accordance with another non-limiting embodiment of the present invention, respectively in contracted and expanded orientations.

Reference is now made to FIGS. 5A-5B, which illustrate a cage device 10D, constructed and operative in accordance with another non-limiting embodiment of the present invention, with like elements being designated by like numerals. This embodiment is similar to that of FIGS. 4A-4B, except that the central common ratchet wall 24 is internal, and the outer sides of expanding members 12 and 18 ratchet against the inner ratcheted surface of wall 24.

In both of the embodiments of FIGS. 4A-5B, the movable segments 12 and 18 may be expanded until a certain point where they are mechanically blocked by a lip, or similar arrangement, as is now described with reference to FIGS. 6A, 6B and 7A-7C.

Figures 6A, 6B:
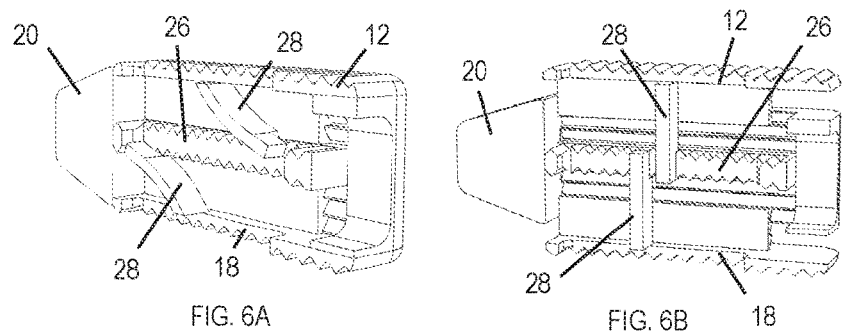
FIGS. 6A-6B are simplified illustrations of a cage device, constructed and operative in accordance with another non-limiting embodiment of the present invention, respectively in contracted and expanded orientations, and including one or more internal pawls and ratchet bars.

In these embodiments, in addition to the ratchet system located on one or both sides or walls of the cage device, another internal ratchet is provided transverse to the other ratchets. For example, as seen in FIGS. 6A-6B, a longitudinal ratchet bar 26 is disposed inside the device extending from the inner face of the tapered nose 20 to the rear of the device. More than one ratchet bar may be used. A ratchet pawl 28 extends (is cantilevered) from one of the expanding members 12 and 18 (in the illustrated embodiment there are two flexible pawls 28, one extending from each of the members 12 and 18) for engaging with the ratchet teeth of ratchet bar 26. In the contracted position of FIG. 6A, the ratchet pawls 28 are curved; in the extended position of FIG. 6B, the ratchet pawls 28 are straight. The additional internal ratchet 26/28 adds a supplementary element of locking, to the point of a possible geometric lock. This enables using a weaker ratchet on the sides, e.g., with smaller teeth, and reduces the forces needed to expand the cage against the side ratchets.

Figures 7A, 7B, 7C:
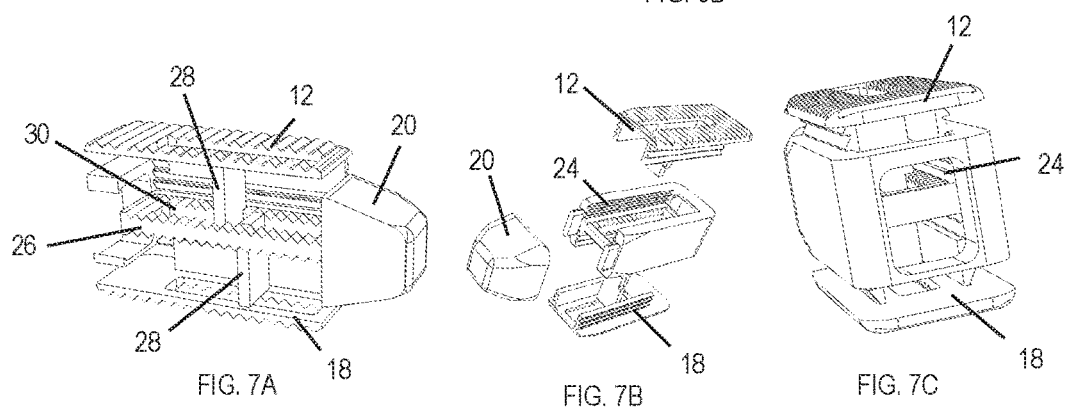
FIGS. 7A-7C are simplified pictorial, exploded and pictorial illustrations of another cage device with one or more internal pawls and ratchet bars.

In the embodiment of FIGS. 7A-7C, the longitudinal ratchet bar 26 is formed with a window 30 and the pawls 28 engage the ratchet bar 26 in teeth formed in window 30.

Figure 8:
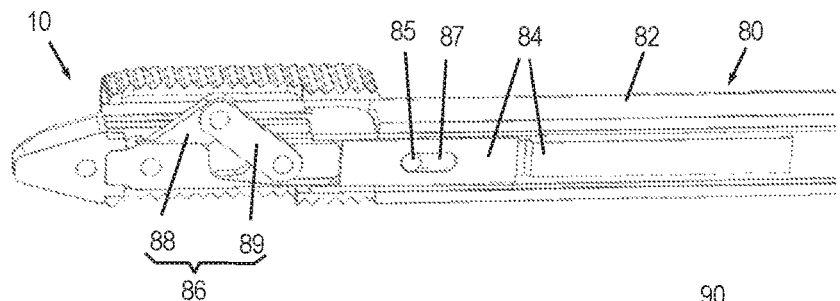
FIG. 8 is a simplified, cutaway illustration of an expansion tool for expanding any of the cage devices, in accordance with another non-limiting embodiment of the present invention.

Reference is now made to FIG. 8, which illustrates an expansion tool 80 for expanding any of the cage devices, in accordance with another non-limiting embodiment of the present invention. Expansion tool 80 includes a shaft 82, a pusher element 84 and an expansion member 86. Pusher element 84 may be an elongate rod or shaft that moves axially inside shaft 82 and which is connected to a proximal end of expansion member 86. Pusher element 84 may include a pin 85 that slides in a channel 87. The pin 85 serves as a guide during the movement of pusher element 84 and may become locked in place at the ends of channel 87 to temporarily lock the expansion member 86 in the contracted or expanded state.

Expansion member 86 may include a pair of links 88 and 89 which are pivotally connected to each other. Each of the links 88 and 89 is also pivotally connected to portions of the expansion tool 80. In the contracted state, links 88 and 89 lie flat; in the expanded state (shown in FIG. 8 after having been pushed distally by expansion member 86) the links 88 and 89 are forced upwards in the sense of the drawing to move the ratcheted members upwards, thereby expanding the cage device.

Expansion tool 86 is inserted through the coupling port 29 (not marked in FIG. 8, but seen in FIGS. 3A-3B).

Reference is now made to FIGS. 9A-9D are simplified illustrations of an insertion tool 90 for holding and inserting any of the cage devices, in accordance with another non-limiting embodiment of the present invention.

Insertion tool 90 may include an outer shaft 92 and one or more inner shafts, such as first and second inner shafts 94 and 96. The inner shafts move longitudinally inside outer shaft 92. The inner shafts may be telescoping, that is, second inner shaft 96 slides inside first inner shaft 94. In the illustrated embodiment, resilient tabs 93 are provided near the distal end of insertion tool 90 (the tabs may be attached of any of the inner shafts or to the outer shaft). The outer shaft 92 may be provided with flared ends 95 for interfacing or locking with the rear face of cage device 10.

Figure 9A:
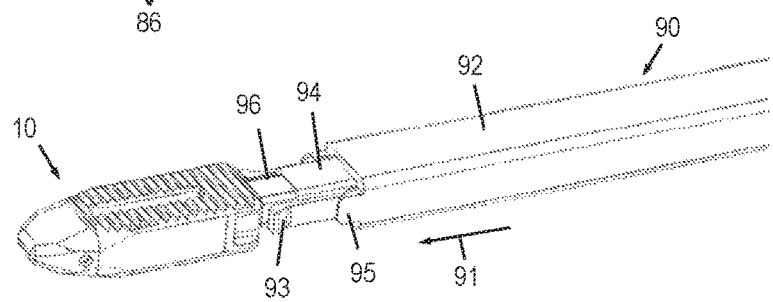
FIGS. 9A-9D are simplified illustrations of an insertion tool for holding and inserting any of the cage devices, in accordance with another non-limiting embodiment of the present invention.

In FIG. 9A, the second inner shaft 96 is inserted into the coupling port 29 (not marked in FIG. 8, but seen in FIGS. 3A-3B) of cage device 10. The insertion direction is indicated by arrow 91.

Figure 9B:
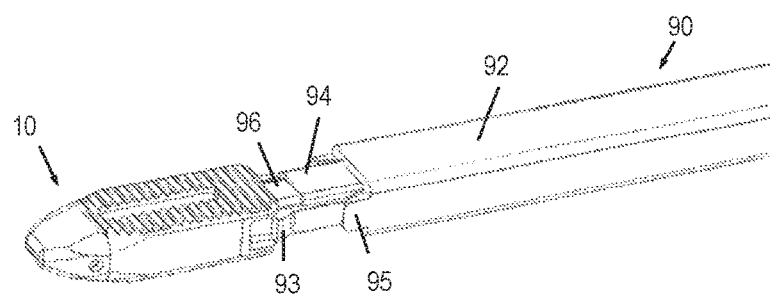

In FIG. 9B, continued distal movement of the tool 90 brings resilient tabs 93 closer of the rear face of cage device 10.

Figure 9C:
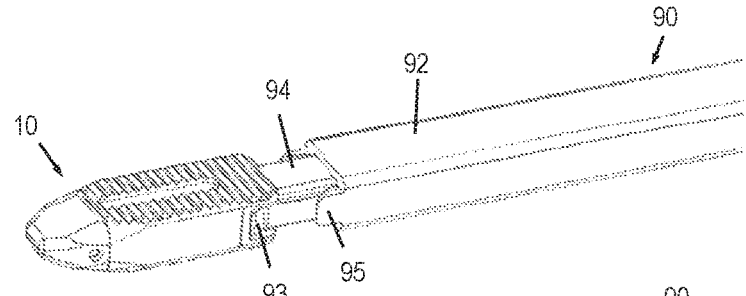

In FIG. 9C, continued distal movement of the tool 90 causes resilient tabs 93 to positively mate (such as by a snap connection) with the rear face of cage device 10. At this point, the cage device is attached to insertion tool 90, but the cage device 10 is free to pivot towards either side of tool 90. The freedom to pivot may enable inserting the cage device 10 in hard-to-reach places in the patient anatomy.

Figure 9D:
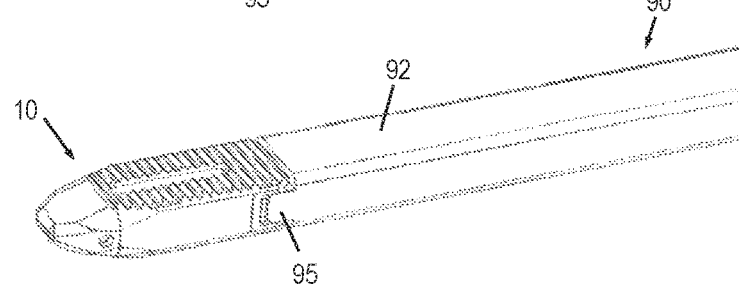

In FIG. 9D, if it is desired to lock the cage device 10 from pivoting to the sides, tool 90 may be pushed more distally so that the flared ends 95 lock with the rear face of cage device 10.

The expansion or insertion tool may be used to introduce bone graft or bone substitute material or other substances into the port and/or expanded, hollow portions of the cage device after cage expansion.

Figure 10:
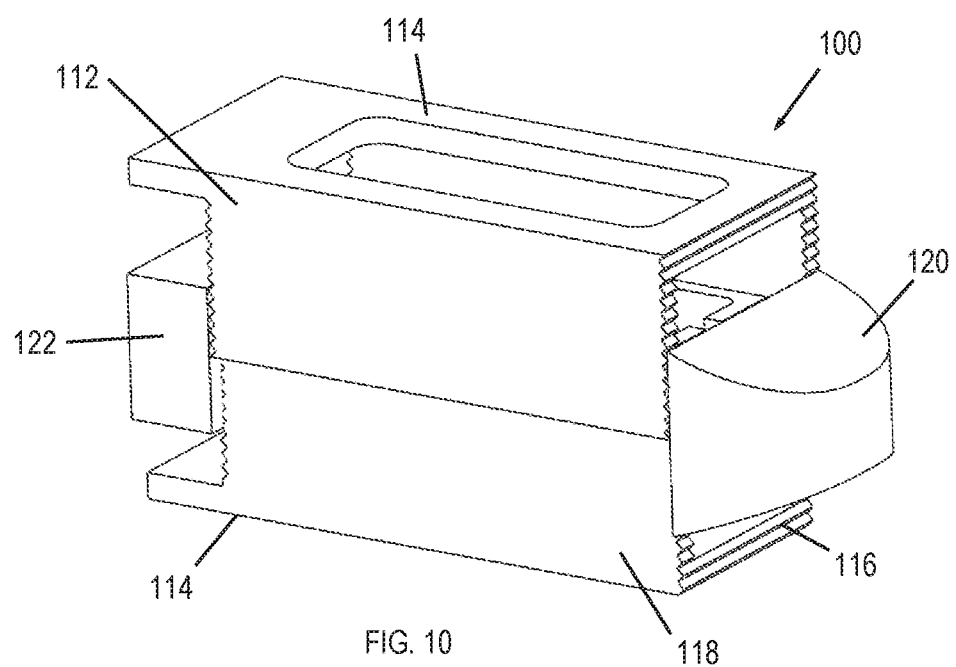
FIG. 10 is a simplified illustration of a cage device, constructed and operative in accordance with another non-limiting embodiment of the present invention.

Reference is now made to FIG. 10, which illustrates a cage device 100, in accordance with a non-limiting embodiment of the present invention.

Similar to the embodiment of FIG. 1, cage device 100 includes a first support member 112, a second support member 118, and bone contact surfaces 114 from which depend side surfaces that are provided with ratchet teeth 116. In this embodiment, the side surfaces are either the front (also called leading or distal) face or the rear (also called trailing or proximal) face, or both the front and rear faces. Support members 112 and 118 can be planar as shown, but alternatively may have other shapes, such as but not limited to, crescent, round, oval, trapezoid or any other shape. Cage device 100 may include a tapered nose section 120 for assisting insertion in the disc space or other places. Cage device 100 may include a trailing portion 122.

What is claimed is:

1. A cage device comprising:
    a first support member which has a bone contact surface and from which depend side surfaces that are provided with ratchet teeth;
    wherein said first support member ratchets with a ratchet member, which in turn ratchets with a ratchet wall, such that said first support member and said ratchet member are movable independently of each other and form a multiple sliding mechanical mechanism, and wherein ratchet elements of said first support member and said ratchet member are not oriented in same directions.

2. The cage device according to claim 1, wherein ratchet elements of said first support member and said ratchet member are all oriented in same directions, thereby permitting movement in one direction only.

3. The cage device according to claim 1, wherein said ratchet member comprises a second support member, and said first support member and said second support member are ratcheted with each other by means of one or more ratchet walls extending from said second support member.

4. The cage device according to claim 1, wherein said first support member ratchets telescopically with said ratchet member.

5. The cage device according to claim 1, wherein said first support member ratchets telescopically with a first internal ratchet member and said first internal ratchet member ratchets telescopically with a second internal ratchet member.

6. The cage device according to claim 1, further comprising a coupling port for inserting therein a tool.

7. The cage device according to claim 1, further comprising an expansion tool for moving said first support member in an expansion direction.

8. The cage device according to claim 7, wherein said expansion tool comprises a shaft, a pusher element and an expansion member.

9. The cage device according to claim 1, further comprising an insertion tool for holding and inserting said cage device.

10. The cage device according to claim 9, wherein said insertion tool comprises an outer shaft and one or more inner shafts.

11. A cage device comprising:
a first support member which has a bone contact surface and from which depend side surfaces that are provided with ratchet teeth;
wherein said first support member ratchets with a ratchet member, which in turn ratchets with a ratchet wall, such that said first support member and said ratchet member are movable independently of each other and form a multiple sliding mechanical mechanism, wherein said first support member ratchets non-telescopically with said ratchet member.

12. A cage device comprising:
a first support member which has a bone contact surface and from which depend side surfaces that are provided with ratchet teeth;
wherein said first support member ratchets with a ratchet member, which in turn ratchets with a ratchet wall, such that said first support member and said ratchet member are movable independently of each other and form a multiple sliding mechanical mechanism, and further comprising an internal ratchet transverse to said first support member.

13. The cage device according to claim 12, wherein said internal ratchet comprises a ratchet pawl that ratchets with a longitudinal ratchet bar.

14. The cage device according to claim 13, wherein said longitudinal ratchet bar is formed with a window and said pawl engages said ratchet bar in teeth formed in said window.

* * * * *